(12) United States Patent
Hudry et al.

(10) Patent No.: US 8,647,687 B2
(45) Date of Patent: Feb. 11, 2014

(54) ISOAMYL ACETATE FOR WEIGHT MANAGEMENT

(75) Inventors: Julie Laure Hudry, Lausanne (CH); Johannes Le Coutre, Pully (CH); Alexander Erin, Epalinges (CH)

(73) Assignee: Nestec S.A., Vevey (CH)

(*) Notice: Subject to any disclaimer, the term of this patent is extended or adjusted under 35 U.S.C. 154(b) by 285 days.

(21) Appl. No.: 13/003,666

(22) PCT Filed: Jul. 9, 2009

(86) PCT No.: PCT/EP2009/058725
§ 371 (c)(1),
(2), (4) Date: Apr. 4, 2011

(87) PCT Pub. No.: WO2010/003997
PCT Pub. Date: Jan. 14, 2010

(65) Prior Publication Data
US 2012/0040046 A1    Feb. 16, 2012

(30) Foreign Application Priority Data

Jul. 11, 2008   (EP) .................................. 08160200

(51) Int. Cl.
| | |
|---|---|
| A23K 1/18 | (2006.01) |
| A23G 3/20 | (2006.01) |
| A23F 3/16 | (2006.01) |
| A23L 2/00 | (2006.01) |
| A23L 2/38 | (2006.01) |
| A61K 38/00 | (2006.01) |
| A61P 3/04 | (2006.01) |
| A01N 65/00 | (2009.01) |
| A61K 36/00 | (2006.01) |
| A61K 8/97 | (2006.01) |
| A61Q 11/00 | (2006.01) |
| A61K 47/00 | (2006.01) |

(52) U.S. Cl.
USPC ............ 426/2; 426/103; 426/330.3; 426/590; 514/4.8; 424/725; 424/777; 424/58; 424/439

(58) Field of Classification Search
USPC .......................... 426/2; 424/153, 317, 439, 58
See application file for complete search history.

(56) References Cited

U.S. PATENT DOCUMENTS

| | | |
|---|---|---|
| 4,497,798 A | 2/1985 | Lambert |
| 5,728,412 A * | 3/1998 | Fujii et al. ...................... 506/10 |
| 2003/0147938 A1 | 8/2003 | Hirsch |

FOREIGN PATENT DOCUMENTS

| | | |
|---|---|---|
| EP | 1835018 | 9/2007 |
| FR | 2727627 | 6/1996 |
| JP | 2007085498 | 4/2007 |
| KR | 20030039830 | 5/2003 |
| KR | 20060054681 | 7/2006 |
| RU | 2077228 | 4/1997 |
| WO | WO2007110115 | 10/2007 |

OTHER PUBLICATIONS

TOXNET—Isoamyl Acetate. Available online at http://toxnet.nlm.nih.gov on Dec. 3, 2005.*

(Continued)

*Primary Examiner* — Rena Dye
*Assistant Examiner* — Assaf Zilbering
(74) *Attorney, Agent, or Firm* — K&L Gates LLP

(57) ABSTRACT

Described is the use of isoamyl acetate in food compositions for weight management and/or weight control. Further described is a beverage containing isoamyl acetate.

14 Claims, 2 Drawing Sheets

(56) References Cited

OTHER PUBLICATIONS

Compendium of Food Additive Specifications. Available online on www.fao.org; published Jun. 1997.*
Banana Oil. Available online at www.ifood.tv on Sep. 24, 2007.*
Really Useful Fitness Blog. Available online at www.fitfaq.com on Nov. 27, 2004.*
The Merck Index—Isoamyl Acetate. (2006).*
Anonymous, "Banane," Wikipedia L' Encyclopedia Libre [Online], retrieved from the Internet Sep. 17, 2009, XP002546216.
Postel et al., "Gas Chromotographic Determination of Components of Fermented Beverages. II the contents of volatile components in beer," Chemie Mikrobiologie Technologie Der Lebensmittel, vol. 1, 1972, pp. 169-182, XP008111944.
Mandl et al., "Diabetes and Diatbier," Brauwissenschaft, vol. 25, No. 11, 1972, pp. 346-353, XP008111946.
Penton, "Flavor Volatiles in a Fruit Beverage With Automated SMPE," Food Tasting & Analyses, vol. 2, No. 3, 1996, pp. 16-18, XP008112345.
Rujischop et al., "Effects of Retro-Nasal Aroma Release on Satiation," British Journal of Nutrition, vol. 9, No. 5, May 2008, pp. 1140-1148, XP008096527.

* cited by examiner

ISOAMYL ACETATE FOR WEIGHT MANAGEMENT

FIELD OF THE INVENTION

The present invention relates to the field of weight management and weight control. Aspects of the present invention relate in particular isoamyl acetate which consumed prior to a meal reduces appetite and facilitates weight management. The present invention also relates to a beverage comprising isoamyl acetate as well as to the use of isoamyl acetate in food compositions for weight management and weight control.

BACKGROUND ART

It is known that some sensory properties of food can enhance satiety and consequently reduce appetite and subsequent food intake. It has been reported by de Wijk et al (2004): Amount of ingested custard dessert as affected by its color, odor, and texture, Physiol. Behav. 82:397-403 that intake decreased as food thickness increased. In the same study, a lower intake was also observed when eliminating food odors using a nose clip. Other studies have been carried out to investigate the impact of meals composed of more or less variety in sensory properties (Bellisle and Le Magnen (1981): The structure of meals in humans: Eating and drinking patterns in lean and obese subjects, Physiol. Behav. 27:649-58; Rolls et al (1981): Variety in a meal enhances food intake in man, Physiol. Behav. 26:215-21; Berry et al (1985): Sensory and social influences on ice cream consumption by males and females in a laboratory setting, Appetite 6:41-5). Varying flavor has shown diverse results.

In general, the results show that increased variety increases food and energy intake. Further, it has been shown that prior olfactory stimulation of a given food (smelling the food) without ingestion could lead to a reduction of appetite for subsequent intake of this specific food (Rolls and Rolls (1997): Olfactory sensory-specific satiety in humans, Physiol. Behav. 61:461-73).

However, opposite patterns were also reported by Fedoroff et al (2003): The specificity of restrained versus unrestrained eaters' responses to food cures: general desire to eat, or craving for the cued food? Appetite 41:7-13. In their studies, the authors found that prior exposure to food smells (pizza or cookies) enhances appetite for the related food (pizza or cookies). Taken together, these findings highlight the importance of olfactory stimulation in the regulation of appetite.

Decreased appetite through inhalation of odorants has been demonstrated by Hirsch and Gomez (1995): Weight Reduction Through Inhalation of Odorants, J. Neurol. Orthop. Med. Surg. 16: 28-31. The authors tested the impact of inhaling a blend of sweet food aromas on food intake in an obese population. Participants were instructed to sniff a plastic nasal inhaler each time they were hungry and to record how often they sniffed over a 6-month period. Results showed a positive correlation between the frequency of using the inhaler and weight loss. The benefit of the inhaler was attributed to a reduction of food cravings leading to a general decrease of appetite and consequent food intake. However, in the absence of a negative control blend, it remains difficult to attribute this impact to a specific aroma or to a placebo effect.

US 2003/0147938 A1 describes sweet and salty tastants which are applied to a food stuff which is then consumed. Hereby the satiation effect of the food stuff is extended to achieve appetite suppression and a reduction in caloric intake.

From consumer's view, however, it would be more desirable to have a satiety feeling just before consumption of the food which would make weight management much easier.

Thus, it is object of the invention to provide a more effective approach for conveniently suppress appetite prior to consumption of a regular meal helping in the management of weight control during a weight reduction diet or to avoid unnecessary weight gain.

SUMMARY OF THE INVENTION

Accordingly, this object is achieved by means of features of the independent claims. The dependent claims further define preferred embodiments of the present invention.

The present invention describes the use of isoamyl acetate in food compositions for weight management and/or weight control.

The food compositions may be enriched in isoamyl acetate.

Food compositions comprising isoamyl acetate may also be used to treat or prevent overweightness and/or obesity.

"Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30.

"Body mass index" or "BMI" means the ratio of weight in Kg divided by the height in metres, squared.

"Overweight" is defined for an adult human as having a BMI between 25 and 30.

The food composition of the present invention may be to be administered prior to a meal.

"Prior to a meal" includes the time frame from 1 hour before the meal to the meal. For example, the food composition may be to be administered 30 minutes or less before a meal.

It has been surprisingly found, at the behavior level, that prior consumption of a food composition containing isoamyl acetate reduces subsequent appetite for the regular meal providing a convenient feeling of satiety.

Furthermore, the appetite reduction achieved does not have an impact on any change in pleasure and perceived intensity of the subsequent meal.

For example isoamyl acetate or food compositions comprising isoamyl acetate may be used to support a weight reduction diet. Hence, the food composition of the present invention or isoamyl acetate may be to be administered to a person and/or a patient during a weight reduction diet.

The inventors were surprised to find that the consumption of isoamyl acetate decreases the wanting of food while maintaining the liking of it.

The present invention provides a beverage comprising a liquid base and isoamyl acetate.

Further, according to the present invention, isoamyl acetate may be used for an agent for weight management and/or weight control.

The invention will now be described in more detail by means of illustrative embodiments.

DETAILED DESCRIPTION OF THE PRESENT INVENTION

Figure 1:
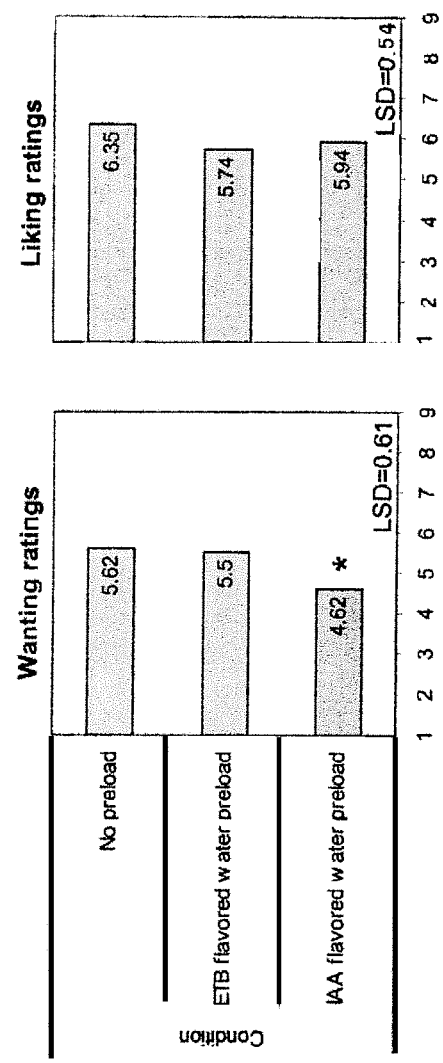
FIG. 1 shows schematic representations of wanting ratings and liking ratings obtained in a clinical trial with ethyl butyrate flavored water and isoamyl acetate flavored water.

According to the present invention, isoamyl acetate is used in food compositions suitable for weight management and/or weight control.

Isoamyl acetate can be used either as natural extract or may be synthesized chemically.

Isoamyl acetate has the formula:

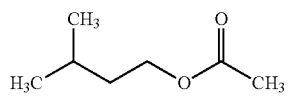

Isoamyl acetate may be for example found naturally in fruits such as banana, pear and apple; and in other food products such as beer, butter and cocoa bean.

Depending on the final use of the food composition, isoamyl acetate can be used as a mixture or blend of various aroma compounds. In a preferred embodiment, a mixture of aroma compounds having fruit flavor qualities is used.

In particular, isoamyl acetate may be used alone or in combination with other aroma compounds, for example 2-methyl-1-propanol, acetal, hexanal, butyl acetate, E-2-hexanal, 2-pentanol acetate, butyl butyrate, limonene, isoamyl butyrate or eugenol.

The food compositions of the present inventions may be enriched in isoamyl acetate.

The food composition of the present inventions may contain isoamyl acetate in an amount of 0.001 µg to 1,000,000 µg per 100 g of the composition. For example, the composition may contain isoamyl acetate in an amount of 1.0 µg to 500,000 µg or of 1,000 µg to 50,000 µg per 100 g of the composition.

In a preferred embodiment of the invention, the food composition is a low-calorie food product which is highly accepted by the consumer. Non-limiting examples of the food products are beverages, confectionary and diary products.

According to the present invention, a beverage is provided comprising a liquid base and isoamyl acetate.

A beverage according to the invention can be any drink which is conveniently consumed before the regular meal. The drink provides a pleasant satiable effect so that the consumer is already at least partly satiated when taking the regular meal.

According to the invention, isoamyl acetate is dissolved in the liquid base. The liquid base in which the aroma compound is dissolved, may be any low-calorie liquid suitable for weight reduction and weight management. Examples of the liquids are water, carbonated water, fruit juice, lemonade, coffee, tea and skimmed milk. Preferably, water such as mineral water is used for the liquid. The liquids can be also carbonated, if appropriate.

In a particular embodiment of the invention, the beverage is a flavored water added with isoamyl acetate. The water may be a mineral water having a banana flavor.

In a preferred embodiment of the present invention, the beverage contains isoamyl acetate in an amount of 0.001 µg to 1,000,000 µg per 100 ml liquid. More preferred, the composition contains isoamyl acetate in an amount of 1.0 µg to 500,000 µg per 100 ml liquid. Most preferred, the composition contains isoamyl acetate in an amount of 1,000 µg to 50,000 µg per 100 ml liquid.

If desired, a suitable amount of sweetening agents, for example sugar or sugar substitutes or non-caloric sweeteners may be also dissolved in the liquid. Those skilled in the art will understand that the amount of sweetening agent to be used can vary based on the nature of the sweetening agent and on the intended purpose of the composition. Preferably, the amount of these sweetening agents is in the range of 0.1 to 2.0% w/v, more preferred 0.5 to 1.5% w/v if the sweetening agent is a sugar. On the other hand, the amounts vary depending on the non-caloric sweeteners used. For example, the amounts are 300 to 500 times less if the sweetening agent is saccharin, 200 times less if the sweetening agent is aspartame or 6200 times less if the sweetening agent is sucralose.

If desired, a suitable amount of other nutrients selected from the group consisting of vitamins, minerals, edible fibers or bioaffecting agent (such as caffeine) may be dissolved or encapsulated in the liquid in an amount corresponding to a certain percentage of the U.S. Recommended Daily Allowance (RDA). For example, US RDA of the nutrients from the vitamin group ranges from 2 µg to 550 mg daily for the average adult. These additional nutrients can make up from about 0 to 20% w/v thereof, more particularly in the range of about 0.01 to 5% w/v thereof.

In a preferred embodiment, the beverage is bottled and air-tightly sealed according to standard procedures. Advantageously, the beverage can be provided in the ready-to-drink format.

According to the present invention, isoamyl acetate is used as an agent suitable for weight management and/or weight control.

As mentioned beforehand, isoamyl acetate can, when consumed prior to the regular meal, remarkably reduce appetite so that the consumer is already at least partially satiated. At the same time the consumer will like the meal similarly as if he had not consumed isoamyl acetate beforehand. With the consumption of isoamyl acetate the wanting of food is reduced while the liking of food is maintained.

Consequently, less of the regular meal is actually consumed resulting in a significantly reduced calorie intake while the pleasure perceived from the meal remains the same.

Isoamyl acetate can be conveniently consumed in combination with a food product which is usually well accepted by the consumer.

The food product of the present invention may be a food product intended for human consumption or an animal food product. For example, the product may be a nutritional composition, a nutraceutical, a drink or a food additive.

Typical examples of food products include beverages, confectionary, dairy products, ready-to-eat meals, desserts, ready-to-drink formulas, infant feeding formulas, preferably in low-calorie format.

A convenient form of consuming isoamyl acetate is to dissolve same in a liquid base. In principle, any low-calorie liquid suitable for weight reduction and weight management may be used as liquid base. Examples of the liquids are water, carbonated water, fruit juice, lemonade, coffee, tea and skimmed milk. Preferably, water such as mineral water is used for the liquid. The liquids can be also carbonated, if appropriate.

In a preferred embodiment of the invention, the isoamyl acetate is consumed as a flavored water. Isoamyl acetate is preferably consumed with water or water based beverages, such as mineral water, carbonated water, functional water, fruit juice or sodas.

In the following, the invention is further illustrated by the examples which are not intended to limit the present invention thereto.

EXAMPLES

Example 1

Preparation of Flavored Water for Clinical Trial

Isoamyl acetate was combined with 0.5% w/w sucrose (Fisher Scientific) and dissolved in bottled mineral water (Vittel, Nestlé waters, France). Isoamyl acetate was provided as liquid concentrate supplied by Sigma-Aldrich (Steinheim, Germany). The final concentration of isoamyl acetate was 16 ppm.

Example 2

Clinical Trial

A clinical trial with 17 healthy participants was conducted to investigate the neural correlates of flavor reward in terms of "Liking" (or pleasure) and "Wanting" (or appetite). Seventeen participants rated flavored waters in different conditions while their brain electrical activity was monitored using electro-encephalography. Waters were flavored either with isoamyl acetate (described as banana) or ethyl butyrate (described as strawberry). Experimental conditions consisted in the ratings of the 2 flavored waters after a preload (prior consumption of a flavored water) or without a preload.

The behavioral results of this clinical trial are summarized in FIG. 1 showing the mean Wanting (or appetite) and Liking (or pleasure) ratings (from 1, not at all to 9, extremely) obtained for the ETB flavored water in the different Preload conditions from 17 participants. As compared to the "No preload" condition, prior consumption of IAA flavored water significantly reduced wanting ratings for subsequent consumption [$F(2,32)=5.44$, $P=0.01$]. This effect was not observed for the ETB flavored water preload and did not affect Linking [$F(2,32)=2.91$, ns] and Intensity ratings [$F(2,32)=2.49$, ns]. IAA: isoamyl acetate; ETB: ethyl butyrate.

At the behavioral level, it has been discovered that prior consumption of water flavored with isoamyl acetate reduced subsequent appetite for water flavored with ethyl butyrate. Importantly, this effect was not reciprocal (ethyl butyrate had no impact on appetite for isoamyl acetate flavored water). In addition, the reduction of appetite by isoamyl acetate was obtained without any change in pleasure and perceived intensity for the subsequent food.

Example 3

Preparation of Flavored Water for Consumer Study

Banana flavor was combined with 0.5% w/w sucrose (Fisher Scientific) and dissolved in bottled mineral water (Vittel, Nestlé waters, France). Banana flavor was provided as liquid concentrate supplied by Givaudan (Vernier, Switzerland). Banana flavor was a complex mixtures of aroma compounds including isoamyl acetate. The final concentration of banana was 0.05%.

Example 4

Consumer Study

A consumer study was conducted in 112 participants in order to verify our previous discovery that isoamyl acetate has a satiating impact and therefore can moderate appetite for further food consumption. A design similar as the one previously used in the clinical trial (see above) was applied for Liking, Wanting and Intensity ratings, but we included an additional control condition (unflavored water) and additional flavored preloads. Waters were combined with food-grade complex aromas of banana, strawberry and vanilla provided by flavor houses. Only banana contained isoamyl acetate in its formulation.

Figure 2:
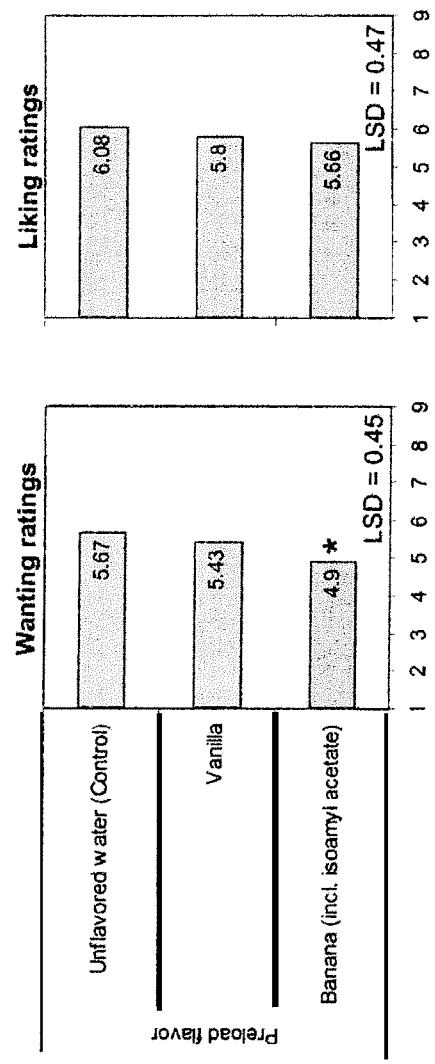
FIG. 2 shows schematic representations of wanting rating and liking ratings obtained in a consumer study with banana flavored (including isoamyl acetate) water, vanilla flavored water and unflavored water.

The outcome of the consumer study is shown in FIG. 2 showing the mean 'Wanting' (or appetite) and 'Liking' (or pleasure) ratings (from 1, not at all to 9, extremely) obtained for the strawberry flavored water in the different preload conditions from 112 consumers. As compared to the vanilla and control conditions, prior consumption of banana flavored (including isoamyl acetate) water significantly reduced wanting ratings for subsequent consumption. This effect did not affect Liking and Intensity ratings.

It has been found that prior consumption of banana flavored water reduced appetite for subsequent consumption of strawberry flavored water (as compared with prior consumption of unflavored water). A similar non significant pattern was obtained for vanilla flavored water. As for the previous study, this effect of banana flavor on appetite was one-sided and specific to the Wanting dimension since Intensity and Liking scores were not affected.

The invention claimed is:

1. A method for weight management in an individual comprising administering a food composition comprising isoamyl acetate to the individual.

2. Method in accordance with claim 1, wherein the food composition is administered before a meal.

3. Method according to claim 1 wherein the food composition comprising isoamyl acetate provides a characteristic selected from the group consisting of reducing appetite relative to a food composition not including isoamyl acetate, enhancing satiation relative to a food composition not including isoamyl acetate, and enhancing the feeling of satiety relative to a food composition not including isoamyl acetate.

4. Method according to claim 1, wherein the food composition comprising isoamyl acetate reduces the desire for a subsequent meal relative to a food composition not including isoamyl acetate while maintaining food enjoyment of a subsequent meal relative to a food composition not including isoamyl acetate.

5. Method according to claim 1 wherein isoamyl acetate is used in combination with another aroma compound selected from the group consisting of 2-methyl-1-propanol, acetal, hexanal, butyl acetate, E-2-hexanal, 2-pentanol acetate, butyl butyrate, limonene, isoamyl butyrate, eugenol and combinations thereof.

6. Method according to claim 1 wherein the food composition is a food product selected from the group consisting of beverages, confectionary, dairy products, ready-to-eat meals, desserts, ready-to-drink formulas and infant feeding formulas.

7. Method according to claim 1, wherein the food composition is administered during a weight reduction diet.

8. Method according to claim 1, wherein the food composition is consumed prior to a meal.

9. Method according to claim 1, wherein the food composition is a flavored water.

10. A method for treating obesity and/or overweightness comprising the step of administering a composition comprising isoamyl acetate to a person suffering from same.

11. Method according to claim 1, wherein the food composition is enriched in isoamyl acetate to have an amount of isoamyl acetate of 0.001 μg to 1,000,000 μg per 100 g of the food composition.

12. Method according to claim 1, wherein the food composition is a beverage containing isoamyl acetate in an amount of 0.001 μg to 1,000,000 μg per 100 ml of the beverage.

13. Method according to claim 12, wherein the beverage contains isoamyl acetate in an amount of 1,000 μg to 50,000 μg per 100 ml of the beverage.

14. Method according to claim 12, wherein the beverage consists of water, a sweetening agent and isoamyl acetate.

* * * * *